United States Patent [19]

Shouldice

[11] Patent Number: 4,814,073
[45] Date of Patent: Mar. 21, 1989

[54] DIALYSATE PREPARATION APPARATUS WITH IMPROVED CONTROL

[75] Inventor: David R. Shouldice, Lakewood, Colo.

[73] Assignee: Cobe Laboratories, Inc., Lakewood, Colo.

[21] Appl. No.: 87,146

[22] Filed: Aug. 19, 1987

Related U.S. Application Data

[63] Continuation of Ser. No. 925,885, Oct. 30, 1986.

[51] Int. Cl.$^4$ .............................................. B01D 13/00
[52] U.S. Cl. ................................. 210/85; 210/96.2; 210/321.69; 210/321.71
[58] Field of Search ............... 210/746, 321.71, 85–87, 210/96.2, 321.69

[56] References Cited

U.S. PATENT DOCUMENTS

| | | | |
|---|---|---|---|
| 4,060,485 | 11/1977 | Eaton | 210/321.71 |
| 4,202,760 | 5/1980 | Storey | 210/101 |
| 4,366,051 | 12/1982 | Fischel | 210/321.71 |
| 4,371,385 | 2/1983 | Johnson | 210/321.71 |
| 4,648,043 | 3/1987 | O'Leary | 210/746 |

OTHER PUBLICATIONS

Chem-Tech International/Iwaki brochure on EP Series Pumps, printed 10/82.
Control Engineering, Mar. 1987, advertisement for Foxboro 760 and 761 controllers.

*Primary Examiner*—Benoit Castel
*Assistant Examiner*—Richard D. Jordan

[57] ABSTRACT

Dialysate preparation apparatus for mixing dialysate concentrate with water, the apparatus including a main flow line having one end for connection to a source of water and another end for providing dialysate to a dialyzer, a concentrate flow line having one end for connection to a source of dialysate concentrate and another end connected to a junction on the main flow line for adding concentrate to water in the main flow line, a volumetric pump having a fixed discharge volume per stroke on the concentrate line, a concentrate sensor on the main flow line downstream of the junction providing control signals to the pump to pump concentrate to achieve the desired concentration, and a controller including a comparator to compare the stroke rate with a limit indicating desired operating stroke rate range.

3 Claims, 1 Drawing Sheet

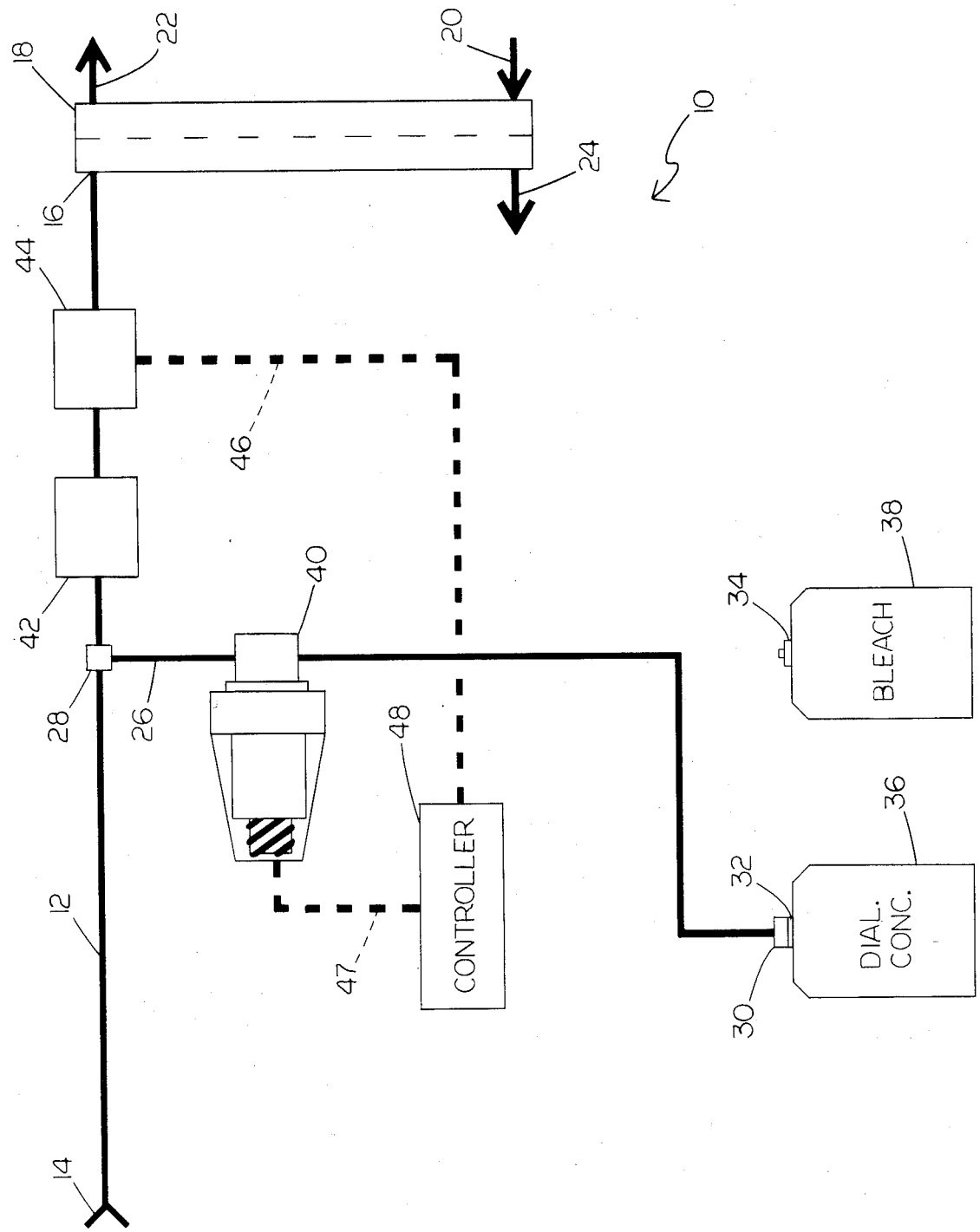

DIALYSATE PREPARATION APPARATUS WITH IMPROVED CONTROL

This application is a continuation of application Ser. No. 925,885, filed Oct. 30, 1986.

FIELD OF THE INVENTION

The invention relates to dialysate preparation apparatus for mixing dialysate concentrate with water.

BACKGROUND OF THE INVENTION

In dialysate preparation apparatus of the type shown in Johnson U.S. Pat. No. 4,371,385 (which is hereby incorporated by reference), water is heated, deaerated, and mixed with dialysate concentrate to continuously provide dialysate supplied to a dialyzer used with a patient. In such apparatus, dialysate is typically pumped to a junction on a main flow line for mixing with water. A downstream conductivity cell is used to sense the conductivity of the mixed solution passing through it (which conductivity is related to the concentration of elements of the dialysate in the water), and this is used in a control loop to control the pump for dialysate concentrate. When such apparatus is disinfected and cleaned, between uses with different patients, bleach or disinfectant are flushed through the hydraulic circuitry of the dialysate preparation apparatus.

SUMMARY OF THE INVENTION

I have discovered that dialysate preparation apparatus can be provided with an additional level of safety (e.g., against adding the wrong chemical) by using a volumetric pump having a fixed discharge volume per stroke to pump concentrate to a main flow line through which water flows, the volumetric pump being controlled in a feedback loop by a concentrate sensor downstream on the main flow line, and by using a controller that compares the stroke rate of the pump with a range of desired operating stroke rates.

In preferred embodiments the concentrate sensor is a conductivity sensor; and the concentrate pump can be connected to either a source of concentrate or a source of cleaning chemical, and the range of desired operating stroke rates for the concentrate excludes the pump rate of the cleaning chemical necessary to achieve the conductivity set point.

Other advantages and features of the invention will be apparent from the following description of a preferred embodiment thereof and from the claims.

DESCRIPTION OF THE PREFERRED EMBODIMENT

The preferred embodiment will now be described.

DRAWING

The drawing is a diagrammatic representation of dialysate preparation apparatus according to the invention.

STRUCTURE

Referring to the drawing, there is shown dialysate preparation apparatus 10, including main flow line 12 having end 14 for connection to a source of water and another end connected to inlet 16 of dialyzer 18, having blood inlet 20 and blood outlet 22 connected to a patient and dialysate outlet 24. Concentrate line 26 is connected at one end to junction 28 on main flow line 12 and at the other end has connector 30 for connection to fitting 32 or fitting 34 on dialysate concentrate (acetate) jug 36 or bleach jug 38.

On concentrate flow line 26 is volumetric diaphragm pump 40 that has a fixed discharge volume per stroke. Downstream of junction 28 on main flow line 12 are mixing chamber 42 and conductivity cell 44. Pump 40 is controlled by a feedback loop based on the conductivity sensed by sensor 44, which loop is indicated by dashed line 46 to controller 48 and dashed line 47 to pump 40 in the drawing. Controller 48 includes a comparator to compare the stroke rate (stroke/time) of pump 40 (i.e., the rate of pulses provided over line 47 to pump 40) with a limit indicating desired operating stroke rate range.

Apparatus 10 also includes a heat exchanger, a combined heater and deaerator, balance chambers (to balance to flow into the dialyzer with that coming out of the dialyzer to control ultrafiltration) and further conductivity cells and a pH sensor all not shown. It also includes a second concentrate supply line (including a pump and jug connector) and junction, mixing chamber and conductivity cell, all upstream of junction 28, to permit bicarbonate to be added using this additional supply line and acid to be added by line 26, to permit use with bicarbonate and acid solutions instead of acetate.

OPERATION

In operation water is provided to flow line 12 at end 14, and dialysate concentrate is pumped by pump 40 to junction 28, in which there is initial mixing of water with the concentrate. Further mixing occurs in mixing chamber 42, which has a vent connected to a vacuum pump (not shown) to remove any gas volatilized from the solution. From mixing chamber 42, the mixed dialysate concentrate/water solution passes through conductivity cell 44, and from there it flows to the dialysate side of the membrane in dialyzer 18. The conductivity sensed by sensor 44 is fed back and used to control pump 40 to achieve a conductivity associated with desired dialysate concentration. The stroke rate of pump 40 is automatically monitored by controller 48, which continuously compares it with a range of desired operating stroke rates for the particular concentrate.

Between use with different patients, the hydraulic circuitry is rinsed with water and flushed with cleaning fluids, some of which may remain in the circuitry for a period of time. "Cleaning fluids" as used herein means bleach or disinfectant or other chemicals which might be flushed through the system. E.g., bleach in jug 38, shown in the drawing, is flushed through the system using pump 40 after connector 30 has been connected to fitting 34 on jug 38.

The continuous monitoring of the stroke rate (i.e., volume/time) by controller 48 prevents use of an improper chemical that could be proportioned to the conductivity set point and cause patient harm. For example, dialysate concentrate is pumped to mix 1 part of it with 34 parts of water, and the conductivity associated with the mixed solution is used as a set point. If the stroke rate of pump 40 is such that it would be pumping 1:20, an alarm is sounded. To pump enough bleach to reach the conductivity set point would require pumping at a stroke rate higher than that associated with 1:20 mixing.

A further advantage is that the feedback loop automatically corrects for changes in concentration of concentrate in jug 36.

OTHER EMBODIMENTS

Other embodiments of the invention are within the scope of the following claims.

What is claimed is:

1. Dialysate preparation apparatus for mixing dialysate concentrate with water, said apparatus comprising
    a main flow line having one end connected to a source of water and another end for connecting to a dialyzer for providing dialysate to said dialyzer,
    a concentrate flow line having one end for connection to a source of dialysate concentrate and another end connected to a junction on said main flow line for adding concentrate to water in said main flow line,
    a volumetric pump having a fixed discharge volume per stroke on said concentrate line so as to pump said concentrate to said main flow line,
    a concentrate sensor means on said main flow line downstream of said junction providing concentration signals indicating concentration of liquid flowing through said concentrate sensor means, and
    a controller means connected to said sensor means for receiving said concentration signals and connected to said pump for providing pump stroke rate control signals to said pump to control the stroke rate of said pump,
    means including said controller means providing with said sensor means and pump a feedback loop in which said pump stroke rate control signals are adjusted so as to achieve a desired concentration corresponding to a desired concentration signal,
    said controller means including a comparator connected to compare a signal indicating commanded stroke rate provided by said controller means with a limit signal indicating desired operating stroke rate range and means to provide an alarm when said signal indicating commanded stroke rate exceeds said limit signal, thereby avoiding pumping of said volumetric pump beyond said desired operating stroke rate range even though commanded to do so based upon said feedback loop.

2. The dialysate preparation apparatus of claim 1 wherein said concentrate sensor means comprises means for sensing conductivity, said concentration signals are conductivity signals, and said desired concentration signal is a conductivity set point corresponding to desired concentration.

3. The dialysate preparation apparatus of claim 2 wherein said concentrate line includes means to connect the concentrate line to a source of concentrate or to a source of cleaning fluid, and said limit signal indicating desired operating stroke rate range for said concentrate does not include a rate permitting pumping of enough said cleaning fluid to achieve said conductivity set point.

* * * * *